US009789077B2

(12) United States Patent
Vuorenmaa et al.

(10) Patent No.: US 9,789,077 B2
(45) Date of Patent: *Oct. 17, 2017

(54) USE OF SAPONIFIED TALL OIL FATTY ACID

(71) Applicant: Hankkija Oy, Hyvinkaa (FI)

(72) Inventors: Juhani Vuorenmaa, Hyvinkaa (FI); Hannele Kettunen, Tervakowski (FI)

(73) Assignee: Hankkija Oy, Hyvinkaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/401,259

(22) PCT Filed: May 14, 2013

(86) PCT No.: PCT/FI2013/050521
§ 371 (c)(1),
(2) Date: Nov. 14, 2014

(87) PCT Pub. No.: WO2013/171371
PCT Pub. Date: Nov. 21, 2013

(65) Prior Publication Data
US 2015/0238454 A1     Aug. 27, 2015

(30) Foreign Application Priority Data
May 14, 2012  (FI) ..................... 20125509

(51) Int. Cl.
| | |
|---|---|
| *A61K 31/19* | (2006.01) |
| *A61K 36/15* | (2006.01) |
| *A23K 20/158* | (2016.01) |
| *A61K 31/20* | (2006.01) |
| *A61K 36/13* | (2006.01) |
| *A23K 50/10* | (2016.01) |
| *A23K 50/15* | (2016.01) |
| *A23L 33/12* | (2016.01) |
| *A23K 50/75* | (2016.01) |
| *A61K 9/00* | (2006.01) |

(52) U.S. Cl.
CPC ............ *A61K 31/20* (2013.01); *A23K 20/158* (2016.05); *A23K 50/10* (2016.05); *A23K 50/15* (2016.05); *A23K 50/75* (2016.05); *A23L 33/12* (2016.08); *A61K 9/0056* (2013.01); *A61K 31/19* (2013.01); *A61K 36/13* (2013.01); *A61K 36/15* (2013.01); *A23V 2002/00* (2013.01); *Y02P 60/56* (2015.11)

(58) Field of Classification Search
CPC ....... A61K 36/15; A61K 31/19; A23K 20/158
See application file for complete search history.

(56) References Cited

U.S. PATENT DOCUMENTS

| | | | |
|---|---|---|---|
| 2,240,365 A | 4/1941 | Dreger | |
| 2,308,431 A | 1/1943 | Brandt | |
| 2,423,236 A | 7/1947 | Harwood et al. | |
| 2,481,356 A | 9/1949 | Segessemann et al. | |
| 2,530,810 A | 11/1950 | Christenson et al. | |
| 2,611,706 A | 9/1952 | Bernhart et al. | |
| 2,736,663 A | 2/1956 | Weber | |
| 2,854,420 A | 9/1958 | Clark et al. | |
| 2,866,739 A | 12/1958 | Ciesielski et al. | |
| 2,894,939 A | 7/1959 | Hampton | |
| 2,941,941 A | 6/1960 | Groll | |
| 2,987,183 A | 6/1961 | Bishop | |
| 3,001,962 A | 9/1961 | Carlston | |
| 3,009,820 A | 11/1962 | Gould | |
| 3,066,160 A | 11/1962 | Hampton | |
| 3,141,897 A | 7/1964 | Crecelius et al. | |
| 3,175,916 A | 3/1965 | Costigliola et al. | |
| 3,194,728 A | 7/1965 | Stump, Jr. | |
| 3,257,438 A | 6/1966 | Wicke et al. | |
| 3,311,561 A | 3/1967 | Anderson et al. | |
| 3,458,625 A | 7/1969 | Ensor et al. | |
| 3,691,211 A | 9/1972 | Julian | |
| 3,830,789 A | 8/1974 | Garrett et al. | |
| 3,887,537 A | 6/1975 | Harada et al. | |
| 3,926,936 A | 12/1975 | Lehtinen | |
| 4,000,271 A | 12/1976 | Kremer et al. | |
| 4,076,700 A | 2/1978 | Harada et al. | |
| 4,118,407 A | 10/1978 | Red et al. | |
| 4,313,940 A | 2/1982 | Pasarela | |
| 4,437,894 A | 3/1984 | Emerson | |
| 4,443,437 A | 4/1984 | Prokosch et al. | |
| 4,810,299 A | 3/1989 | Schilling et al. | |
| 4,810,534 A | 3/1989 | Seaborne et al. | |
| 5,428,072 A | 6/1995 | Cook et al. | |
| 5,460,648 A | 10/1995 | Walloch et al. | |
| 6,020,377 A | 2/2000 | O'Quinn et al. | |
| 6,229,031 B1 | 5/2001 | Strohmaier et al. | |

(Continued)

FOREIGN PATENT DOCUMENTS

| | | |
|---|---|---|
| CA | 2 107 647 A1 | 4/1994 |
| CN | 101461443 A | 6/2009 |

(Continued)

OTHER PUBLICATIONS

Norlin ("Tall Oil", Ullmann's Encyclopedia of Industrial Chemistry, Published Online: Jun. 15, 2000).*
International Search Report for corresponding International Patent Application No. PCT/FI2013/050521 mailed Oct. 9, 2013.
Finnish Search Report for corresponding Finnish Patent Application No. 20125509 mailed Feb. 26, 2013.
Product Data Sheet SYLFAT® 2LTC tall oil fatty acid [online], Arizona Chemical, [last modified Jul. 20, 2009], retrieved Feb. 20, 2013, URL: http://www.arizonachemical.com/Global/PDS/EU_product_data_sheets/SYLFAT%C2%AE%202LTC.pdf.

(Continued)

*Primary Examiner* — Robert Havlin

(74) *Attorney, Agent, or Firm* — Merchant & Gould P.C.

(57) ABSTRACT

The present invention relates to use of a tall oil fatty acid which is modified by saponification in the modulation of microbial population of the animal digestive tract.

14 Claims, 4 Drawing Sheets

(56) References Cited

U.S. PATENT DOCUMENTS

Figure 1A:
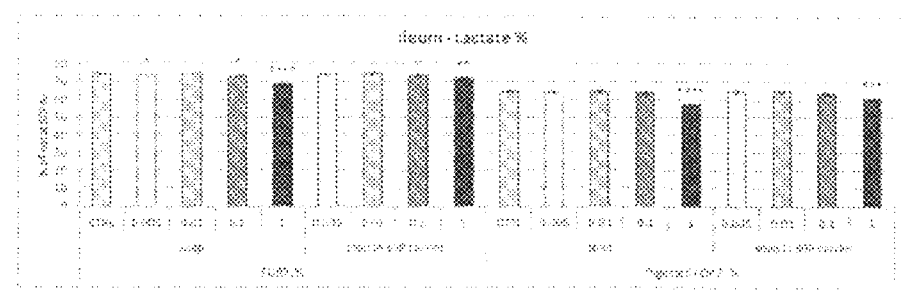

| | | | |
|---|---|---|---|
| 6,608,222 | B2 | 8/2003 | Bonsignore et al. |
| 8,741,171 | B2 | 6/2014 | Swift et al. |
| 9,358,218 | B2 | 6/2016 | Vuorenmaa et al. |
| 9,422,057 | B2 | 8/2016 | Koschberg et al. |
| 2002/0147356 | A1 | 10/2002 | Bonsignore et al. |
| 2002/0183298 | A1 | 12/2002 | Schersl et al. |
| 2003/0144536 | A1 | 7/2003 | Sonnier et al. |
| 2005/0107582 | A1 | 5/2005 | Wong et al. |
| 2005/0203279 | A1 | 9/2005 | Rojas et al. |
| 2006/0021276 | A1 | 2/2006 | Sonnier |
| 2006/0286185 | A1 | 12/2006 | Prokosch |
| 2008/0262251 | A1 | 10/2008 | Sato et al. |
| 2009/0012164 | A1 | 1/2009 | Kelderman |
| 2009/0220638 | A1* | 9/2009 | Pablos Perez .......... C11C 1/025 426/2 |
| 2009/0277972 | A1 | 11/2009 | Kennon et al. |
| 2009/0285931 | A1 | 11/2009 | Shelby et al. |
| 2009/0297687 | A1 | 12/2009 | Ramirez Marco et al. |
| 2011/0081442 | A1 | 4/2011 | Weill et al. |
| 2011/0200570 | A1 | 8/2011 | Mosbaugh et al. |
| 2011/0212217 | A1 | 9/2011 | Herranen et al. |
| 2011/0212218 | A1 | 9/2011 | Herranen et al. |
| 2012/0070516 | A1 | 3/2012 | Tranquil et al. |
| 2015/0164966 | A1 | 6/2015 | Vuorenmaa et al. |
| 2016/0081368 | A1 | 3/2016 | Vuorenmaa et al. |
| 2016/0081952 | A1 | 3/2016 | Vuorenmaa et al. |
| 2016/0089407 | A1 | 3/2016 | Vuorenmaa et al. |
| 2016/0250171 | A1 | 9/2016 | Vuorenmaa et al. |
| 2016/0250269 | A1 | 9/2016 | Rintola et al. |

FOREIGN PATENT DOCUMENTS

| | | |
|---|---|---|
| DE | 101 06 078 A1 | 9/2002 |
| EP | 0 078 152 A1 | 5/1983 |
| EP | 0 146 738 A1 | 7/1985 |
| EP | 1 586 624 A1 | 10/2005 |
| EP | 2 343 061 A1 | 7/2011 |
| FI | 41337 B | 6/1969 |
| FI | 20110371 A | 4/2013 |
| FI | 20120287 A | 4/2013 |
| GB | 955316 A | 4/1964 |
| GB | 2 139 868 A | 11/1984 |
| GB | 2 271 282 A | 4/1994 |
| JP | S60-237008 A | 11/1985 |
| WO | WO 94/16690 A1 | 8/1994 |
| WO | WO 99/10148 A1 | 3/1999 |
| WO | WO 02/02106 | 1/2002 |
| WO | WO 03/024681 A1 | 3/2003 |
| WO | WO 2006/040537 A1 | 4/2006 |
| WO | WO 2008/099051 A2 | 8/2008 |
| WO | WO2008154522 * | 12/2008 .............. A23D 7/00 |
| WO | WO 2009/079680 A1 | 7/2009 |
| WO | WO 2009/106696 A1 | 9/2009 |
| WO | WO 2011/042613 A2 | 4/2011 |
| WO | WO 2011/055018 A2 | 5/2011 |
| WO | WO 2011/080399 A1 | 7/2011 |
| WO | WO 2011/099000 A2 | 8/2011 |
| WO | WO 2012/037297 A1 | 3/2012 |
| WO | WO 2013/060936 A1 | 5/2013 |
| WO | WO 2013/118099 A1 | 8/2013 |
| WO | WO 2013/171370 A1 | 11/2013 |
| WO | WO 2014/184430 A1 | 11/2014 |

OTHER PUBLICATIONS

Extended European Search Report for corresponding European Patent Application No. 13790872.9 mailed Nov. 17, 2015.
Smith, E. et al., "Isopimaric Acid from *Pinus nigra* shows Activity against Multidrug-resistant and EMRSA Strains of *Staphylococcus aureus*", *Phytotherapy Research*, 19(6): 538-542 (2005).
Savluchinske-Feio, S. et al., "Antimicrobial activity of resin acid derivatives", *Appl. Microbiol. Biotechnol.*, 72: 430-436 (2006).
European Search Report for European Patent Application No. 14797471.1 mailed Dec. 6, 2016, 11 pgs.
European Search Report for European Patent Application No. 14797745.8 mailed Dec. 5, 2016, 9 pgs.
European Search Report for European Patent Application No. 14797238.4 mailed Dec. 7, 2016, 10 pgs.
Duncan, D.P., "Tall Oil Fatty Acids", *Naval Stores*, 346-349 (1989).
Gudmundur, B. et al., "Antibacterial, Antiviril and Antifungal Activities of Lipids" in "Lipids and Essential Oils as Antimicrobial Agents", *John Wiley & Sons*, 47-80 (2011).
Van Nevel, C.J. et al., "Effect of Fatty Acid Derivatives on Rumen Methane and Propionate In Vitro[1]", *Applied Microbiology*, 365-366 (1971).
Antila, M. et al., "The fatty acids of tall oil and their ethyl and glyceryl esters as animal fodder ingredients, the chemical and physical properties of the fatty acid fraction and esters prepared from this fraction", *Journal ACTA Agriculureae Scandinavia*, 12: 95-105, 1962, Abstract.
Bannink, A. et al., "A model of enteric fermentation in dairy cows to estimate methane emission for the Dutch National Inventory Report using the IPCC Tier 3 approach", 166-167: 603-618, 2011.
Beauchemic, K.A., et al., "Nutritional management for enteric methane abatement: a review", *Australian Journal of Experimental Agriculture*, 48: 21-27, 2008.
de Graaf et al., "Consumption of tall oil-derived phytosterols in a chocolate matrix significantly decreases plasma total and low-density lipoprotein-cholesterol levels", *British Journal of Nutrition*, 88: 479-488, 2002.
Grainger, C. et al., "Can enteric methane emissions from ruminants be lowered without lowering their production?", *Animal Feed Science and Technology*, 166-167; 308-320, 2011.
Machmüller, A., "Medium-chain fatty acids and their potential to reduce methanogenesis in ruminants", *Agriculture, Ecosystems and Environment*, 112: 107-114, 2006.
Machmüller, A. et al., "Potential of various fatty feeds to reduce methane release from rumen fermentation in vitro (Rusitec)", *Animal Feed Science Technology*, 71: 117-130, 1998.
McGuire, J. et al., "Gas Chromatographic Analysis of Tall Oil Fractionation Products After Methylation with N,N-Dimethylformamide Dimethylacetal", *Journal of Chromatographic Science*, 36: 104-108, 1998.
O'Quinn, P.R. et al., "Effects of modified tall oil and creatine monohydrate on growth performance, carcass characteristics, and meat quality of growing-finishing pigs", *Journal of Animal Science*, 78(9): 2376-2382, 2000.
O'Quinn, P.R. et al., "Effects of modified tall oil versus a commercial source of conjugated linoleic acid and increasing levels of modified tall oil on growth performance and carcass characteristics of growing-finishing pigs", *Journal of Animal Science*, 78(9): 2359-2368, 2000.
O'Quinn, P.R. et al., "Effects of modified tall oil versus conjugated linoleic acid on finishing pig growth performance and carcass characteristics", *KSU Swine Day*, 157-161, 1998.
Patra, A.K., "Effects of Essential Oils on Rumen Fermentation, Microbial Ecology and Ruminant Production", *Asian Journal of Animal and Veterinary Advances*, 6(5): 416-428, 2011.
Polan, C.E. et al., "Biohydrogenation of Unsaturated Fatty Acids by Rumen Bacteria", *Journal of Bacteriology*, 88(4): 1056-1064, 1964.
Snell, F. et al., "Comparative Value of Fatty Acids and Resin Acids of Tall Oil in Soaps", *The Journal of the American Oil Chemist's Society*, 27(8): 289-295, 1950.
Zhou, X. et al., "The Effect of Saturated Fatty Acids on Methanogenesis and Cell Viability of *Methanobrevibacter ruminantium*", *Archaea*, 2013: 1-9, 2013.
"Carboxylic Acids, Fatty Acids From Tall Oil", Kirk-Othmer Encyclopedia of Chemical Technology, Copyright 1999-2014 by John Wiley and Sons, Inc., 4 pages.
"Carboxylic Acids, Fatty Acids from Tall Oil", Kirk-Othmer Encyclopedia of Chemical Technology, Copyright 1999-2014 by John Wiley and Sons, Inc., 4 pgs.
"Explanatory Notes to the Harmonized Commodity Description and Coding System", The Department of Duty Collection of the 25 General Administration of Customs, China Commerce and

(56) References Cited

OTHER PUBLICATIONS

TradePress, published on Jan. 31, 2007, see p. 478: "Tall Oil, Whether or Not Refined". English translation of relevant parts.

* cited by examiner

USE OF SAPONIFIED TALL OIL FATTY ACID

This application is a National Stage Application of PCT/FI2013/050521, filed 14 May 2013, which claims benefit of Serial No. 20125509, filed 14 May 2012 in Finland and which applications are incorporated herein by reference. To the extent appropriate, a claim of priority is made to each of the above disclosed applications.

FIELD OF THE INVENTION

The invention relates to use of a tall oil fatty acid which is modified by saponification.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Generally, there is an increasing demand for ingredients for use in animal feeding that can modulate the microbial population in the animal digestive tract but which are readily available, well tolerated and environmentally friendly.

Fractional distillation of crude tall oil, obtained as a by-product of the Kraft process of wood pulp manufacture, produces distilled tall oil (DTO) which typically comprises over 10% resin acids and less than 90% fatty acids. Further refinement of distilled tall oil produces tall oil fatty acid (TOFA), which is available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

Purpose of the Invention

The purpose of the invention is to provide a new type of modified tall oil fatty acid/feed supplement for use in the modulation of microbial population of the animal digestive tract.

The present inventors have surprisingly found that saponification of TOFA improves the solubility of its components and resin acids in the digestive tract of an animal in particular and significantly increases its effectiveness in the modulation of microbial population of the animal digestive tract.

SUMMARY

Use of a tall oil fatty acid which is modified by saponification according to the present invention is characterized by what is presented in claim 1.

DETAILED DESCRIPTION OF THE INVENTION

FIG. 1a Percentage of lactic acid in the ileal simulation as a response to saponified TOFA and digested saponified TOFA concentrations.

Figure 1B:
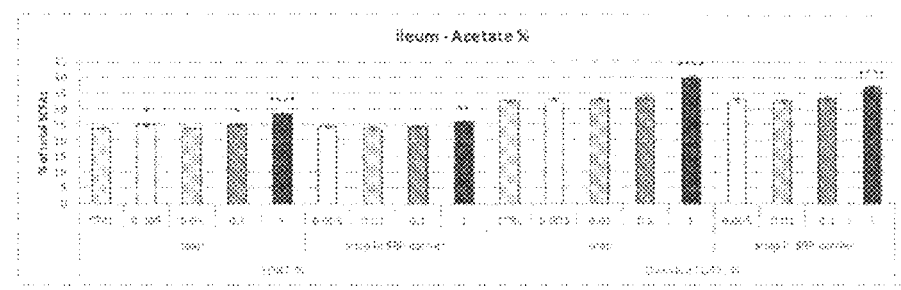

FIG. 1b Percentage of acetic acid in the ileal simulation as a response to saponified TOFA and digested saponified TOFA concentrations.

Figure 1C:
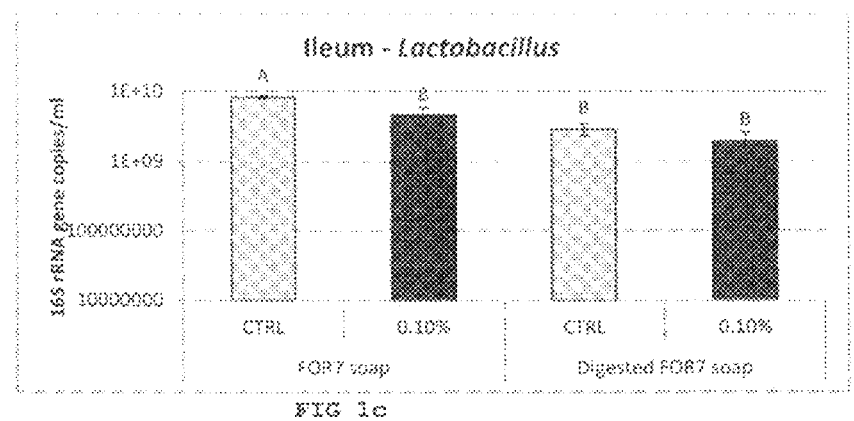

FIG. 1c The number of bacteria of the genus *Lactobacillus* in the ileal simulation samples as a response to saponified TOFA and dried saponified TOFA concentrations.

Figure 1D:
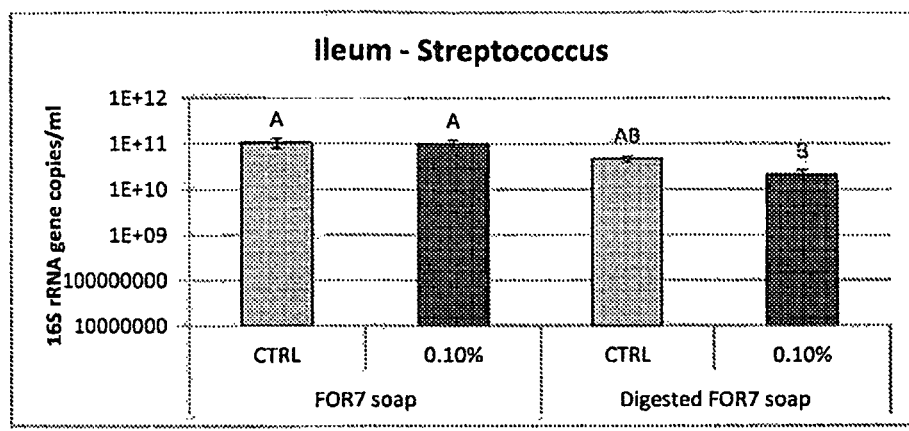

FIG. 1d The number of bacteria of the genus *Streptococcus* in the ileal simulation samples as a response to saponified TOFA and dried saponified TOFA concentrations.

Figure 2A:
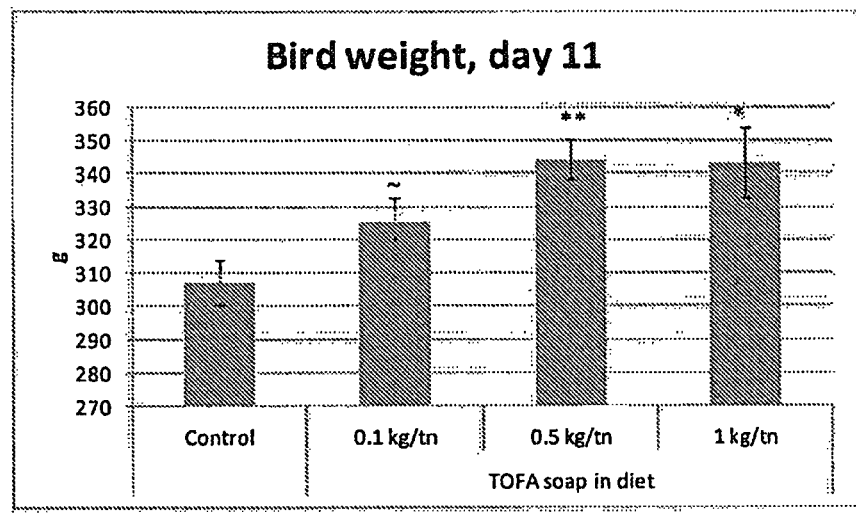

FIG. 2a Weight of the chicks on day 11 as a response to saponified TOFA concentrations.

Figure 2B:
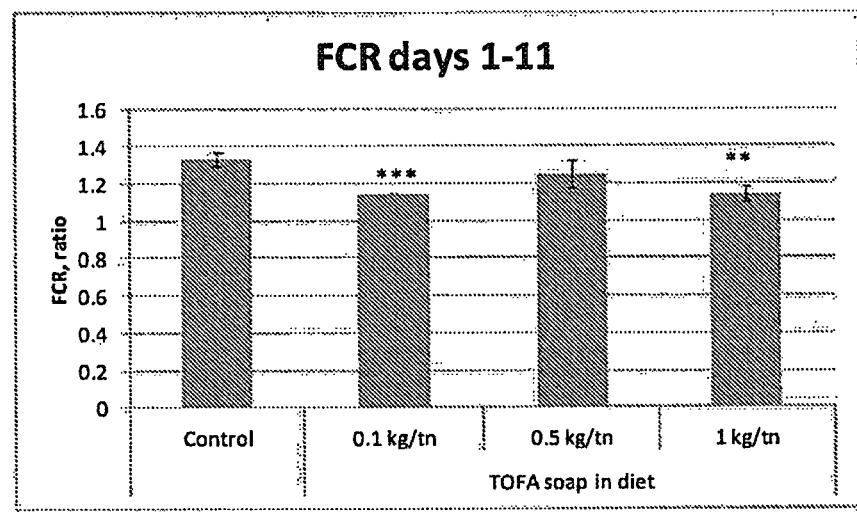

FIG. 2b Feed conversion ratio for days 1-11 as a response to saponified TOFA concentrations.

Figure 2C:
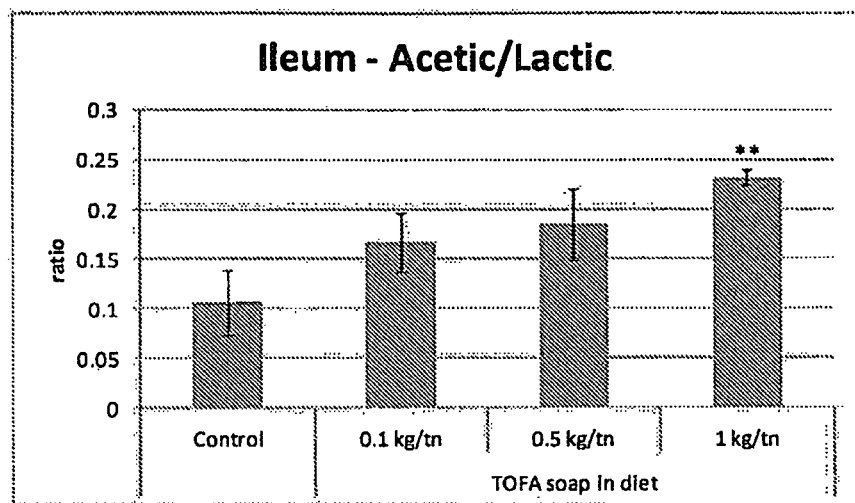

FIG. 2c Ratio between acetic and lactic acids in ileal contents as a response to saponified TOFA concentrations.

Figure 2D:
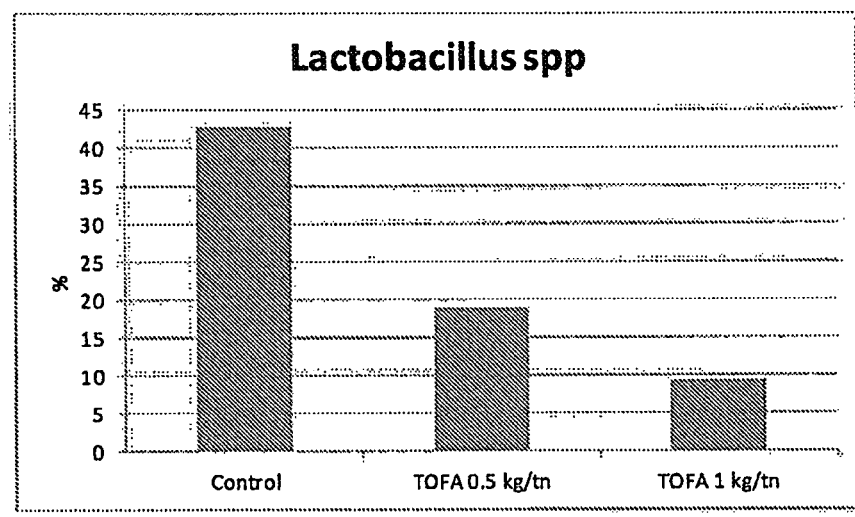

FIG. 2d Proportion of samples with *Lactobacillus* spp count over $1*10^{12}$/g digesta fresh weight as a response to saponified TOFA concentrations.

The present invention is based on the realization that tall oil fatty acid which is modified by saponification can be used in the modulation of microbial population of the animal digestive tract.

The modulation of microbial population of the animal digestive tract is carried from homofermentatine towards heterofermentative metabolical route and in one embodiment of the present invention it improves the feed utilization (improved nutritional value). In another embodiment of the present invention, the modulation of microbial population of the animal digestive tract improves the feed conversion ratio.

The term "tall oil fatty acid" or "TOFA" should be understood as referring to a composition obtained by distillation of crude tall oil and further refinement of distilled tall oil. TOFA or TOFA which is modified by saponification typically comprises 90-98% (w/w) fatty acids. Further, TOFA or TOFA which is modified by saponification may comprise 1-10% (w/w) resin acids.

Resin acids are known to have antimicrobial, including antibacterial, properties. However, the present inventors have found that resin acids of TOFA are poorly soluble in digestive juices and tend to precipitate in the digestive tract of an animal. Therefore their effectiveness in the digestive tract is less than optimal.

The modification of TOFA improves the solubility of its components and resin acids in the digestive tract of an animal.

In this context, the term "tall oil fatty acid which is modified by saponification" or "TOFA which is modified by saponification" should be understood as referring to TOFA that is chemically modified so as to improve the solubility of its components and resin acids in the digestive tract of an animal in particular.

In one embodiment of the present invention, the tall oil fatty acid which is modified by saponification for use according to the present invention comprises 1-10% (w/w) of resin acids.

In one embodiment of the present invention, TOFA or TOFA which is modified by saponification comprises 2-9% (w/w) resin acids.

In one embodiment of the present invention, TOFA or TOFA which is modified by saponification comprises 5-9% (w/w) resin acids.

In this context, the term "resin acids" should be understood as referring to a complex mixture of various acidic compounds comprised by tall oil which share the same basic skeleton including a three-fused ring. The exact composition of the resin acids present in TOFA varies e.g. according to the species of the trees the TOFA is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In one embodiment of the present invention, TOFA or TOFA which is modified by saponification comprises 90-98% (w/w) of fatty acids.

Various processes for the saponification of TOFA using e.g. NaOH or CaOH are known to a person skilled in the art.

In one embodiment of the present invention, the TOFA which is modified by saponification, the TOFA soap, according to the present invention is dried. The TOFA which is modified by saponification can be dried by spray drying, drum drying or by any other known suitable drying method.

The present invention also relates to a feed supplement comprising the tall oil fatty acid which is modified by saponification according to the invention.

In one embodiment of the present invention, the feed supplement is effective in the modulation of microbial population of the animal digestive tract.

In one embodiment of the present invention, the feed supplement comprises a tall oil fatty acid which is modified by saponification and which comprises 1-10% (w/w) resin acids.

In one embodiment of the present invention, the feed supplement comprises a tall oil fatty acid which is modified by saponification and which comprises 2-9% (w/w) resin acids.

In one embodiment of the present invention, the feed supplement comprises a tall oil fatty acid which is modified by saponification and which comprises 5-9% (w/w) resin acids.

In this context, the term "feed supplement" should be understood as referring to a composition that may be added to a feed or used as such in the feeding of animals. The feed supplement may comprise different active ingredients. The feed supplement may be added in the feed in a concentration of 0.0001-5 kg/ton of dry weight, preferably 0.005-1 kg/ton, most preferably 0.01-0.1 kg/ton of the dry weight of the total amount of the feed. The TOFA which is modified by saponification or the feed supplement comprising the TOFA which is modified by saponification according to the invention may be added to the feed or feed supplement as such, or it may in general be further processed as desired.

Further, the TOFA which is modified by saponification or the feed supplement comprising the TOFA which is modified by saponification according to the invention may be added to the feed or feed supplement, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

In one embodiment of the present invention, the feed supplement comprises TOFA which is modified by saponification and which is absorbed into a carrier material suitable for the feed composition such as sugarbeet pulp.

In one embodiment of the present invention, the feed supplement comprises TOFA which is modified by saponification and which is dried.

The present invention also relates to a feed composition comprising the feed supplement according to the invention.

In one embodiment of the present invention, the feed composition comprises the feed supplement in an amount of 0.00001-0.5% (w/w), preferably 0.0005-0.1% (w/w), most preferably 0.001-0.01% (w/w) of the dry weight of the total amount of the feed.

In one embodiment of the present invention, the feed composition comprises the feed supplement in an amount of 0.0005-0.1% (w/w) of the dry weight of the total amount of the feed.

The modified tall oil fatty acid or feed supplement according to the invention is produced by saponification. The method comprises the steps of adding a base to an aqueous TOFA solution and heating the mixture. The mixture is stirred during the heating step. The mixture is heated at a temperature of 80-120° C., preferably at 85-95° C., for a period of 1-3 hours, preferably for 2 hours.

Any base suitable for saponification, such as an alkali metal hydroxide, can be used as the base.

In one embodiment of the present invention, the base that is used is a sodium or potassium hydroxide.

In one embodiment of the present invention, the method of producing a saponified tall oil fatty acid or feed supplement further comprises a step of drying. The dying can be carried out by spray drying, drum drying or by any other known drying method.

The invention also relates to a method of modulating microbial population of the animal digestive tract comprising the step of administering to an animal the tall oil fatty acid which is modified by saponification according to the invention.

In this context, the term "harmful bacteria" should be understood as referring to any bacteria that is capable of affecting the digestive tract or health of an animal in an adverse manner, including competition for nutrients with the host animal. In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species depending on e.g. the health of an animal and on environmental factors.

In this context, the term "animal" should be understood as referring to all kinds of different animals, such as monogastric animals, ruminants, fur animals, pets and aquaculture. Non-limiting examples of different animals, including offspring, are cows, beef cattle, pigs, poultry, sheep, goats, horses, foxes, dogs, cats and fish.

In one embodiment of the present invention, the TOFA which is modified by saponification is administered to an animal in an effective amount.

The present invention has a number of advantages. TOFA is a readily available, natural, low-cost and environmentally friendly material. Further, it is non-toxic and well tolerated. The invention is effective in modulating the composition of the micro-biota in the animal digestive tract to a direction that is beneficial for animal performance. Subsequently, other benefits of the invention are e.g. improved animal productivity, improved feed conversion ratio, higher product quality, uniformity, nutritional value and food and product safety. The invention also allows the production of feed compositions and supplements at low cost.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

This experiment was conducted to study the effect of saponified TOFA soap with 5% resin acids with or without Sugar Beet Pulp (SBP) carrier on the microbial microbial population and fermentation of broiler chick ileum in vitro.

The saponified TOFA was manufactured by adding 140 mg of NaOH (sodium hydroxide) to 1 gram of TOFA, adding enough water to adjust the total dry matter (TOFA) percentage of the mixture to 18-20%, heating the mixture to +90° C., keeping the temperature at +90° C. for 120 minutes, during which time the mixture was gently stirred at 15 min intervals.

Experiment

Ileal contents of 40-days old broiler chicks were used for the simulation media and as inoculants in the simulation models. The trial treatments were prepared from a batch of saponified TOFA soap.

Preparations of TOFA with 5% resin acids were produced:
1. Saponified TOFA (FOR7) with 20% dry matter content An aliquot of the TOFA soap was heated to 90° C., mixed with finely ground SBP powder, and dried to contain 375 g dry TOFA soap/kg.

2. Saponified and digested TOFA (FOR7) Gastrointestinal digestion of the saponified TOFA: Part of the liquid TOFA soap and the carrier-absorbed TOFA soap was digested by a pepsin-HCl—treatment (pH 2.25) followed by a pancreatin bile-acid-NaOH treatment (pH 6.2) in a dilution series. The digestion was made to evaluate whether the products would resist the conditions of the upper gastrointestinal tract before they enter the distal intestine with higher microbial activity.

The simulation was conducted in a total of 160 2-ml plastic microcentrifuge vials, in 1.5 ml volume, with 10 hours simulation time. Samples were tested at four concentrations of the dry matter of TOFA: 0%, 0.005%, 0.01%, 0.01% and 1%.

All the simulation samples were analysed for short chain fatty acids and the total number of microbes. In addition, selected samples were analysed for a number of microbial species or groups by quantitative real-time PCR (qPCR). Ileal simulation samples were analysed for lactobacilli and streptococci.

Results

The results are illustrated in FIGS. 1a-1d. In the ileal simulation model, TOFA soap at 1 kg/ton level increased the concentrations of acetic and propionic acids and decreased the concentration of lactic acid (FIGS. 1b and 1a). This suggests modulation of microbial metabolism from homo-fermentative towards heterofermentative metabolical route, which can be seen as a very positive change improving the feed conversion ratio. TOFA soap amendment at 0.1 kg/ton negatively affected the population numbers of lactobacilli and streptococci (FIGS. 1c-1d), all of which are lactate producers. The total bacterial numbers in the ileum were not affected by the TOFA soap, which may indicate that other bacterial populations were increased as a response to the TOFA soap amendment. Predigestion of the TOFA soap affected many of the studied parameters, while the sugar beet pulp carrier had little effect on the fermentation

Example 2

This experiment was conducted to study the effect of saponified TOFA with 5% resin acids on nutritional value of feed and feed conversion ratio. The saponification of the TOFA was conducted as described in Example 1.

Experiment 240 newly-hatched, male Ross 508 broiler chicks were allocated into 40 open pens, six birds per pen and eight replicate pens per feeding treatment.

TOFA soap with 5% resin acid content was absorbed into ground sugar beet pulp (SBP) carrier and added to the feeds. The feed was wheat-soy-based starter formula. The dietary treatments:
1. Control, no TOFA soap
2. Control+TOFA soap 0.1% (1 kg/ton)
3. Control+TOFA soap 0.05% (500 g/ton)
4. Control+TOFA soap 0.01% (100 g/ton)

Chicks were weighed on days 1, 11, 14, and 17. Feed consumption was measured and feed conversion ratio (FCR) was calculated for the same periods. Daily mortality was recorded.

After day 17, 105 ileal and 105 cecal digesta samples were analysed for short chain fatty acids (SCFAs) with gas chromatography and a number of microbial species or groups by qPCR.

Results

The results are illustrated in FIGS. 2a-2d. Dietary TOFA soap with 5% resin acids, fed at the level of 0.1-1 kg/ton, dose-dependently increased the body weight of broiler chicks on days 8, 11, and 14 (FIG. 2a). FCR was improved by the TOFA soap at 0.1-1 kg/ton, either numerically or statistically significantly (FIG. 2b). TOFA soap at 0.1-1 kg/ton favourably and dose-dependently modulated the small intestinal microbial fermentation from homofermentative to heterofermentative direction (FIG. 2c). Ileal and cecal numbers of Cl. perfringens were not significantly affected by dietary TOFA amendment. TOFA soap at 0.5 kg/tn decreased the frequency of samples with more than $1*10^9$ cells of enterococci or streptococci, or more than $1*10^{12}$ cells of lactobacilli. TOFA soap at 1 kg/ton decreased the frequency of samples with high counts of lactobacilli (FIG. 2d).

The results show that the saponified TOFA modulates the microbial population of the digestive tract of broiler chicks or other species of poultry if given in the feed and improve the feed conversion ratio.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:
1. A method of modulating a microbial population of an animal digestive tract comprising:
forming a feed supplement comprising a saponified tall oil fatty acid comprising resin acids, wherein the saponified tall oil fatty acid comprises 2-10% (w/w) resin acids and 90-98% (w/w) fatty acids, wherein the saponified tall oil fatty acid is formed by combining a tall oil fatty acid with a base forming a mixture, and wherein the mixture is heated to at least 90° C. thereby forming the saponified tall oil fatty acid, and administering the feed supplement to the animal, wherein the concentration of the feed supplement is 0.005 to 1 kg/ton dry weight of the total amount of the feed.

2. The method according to claim 1, further comprising for improving feed utilization.

3. The method according to claim 1, further comprising for improving the feed conversion ratio.

4. The method according to claim 1, wherein the saponified tall oil fatty acid comprises 2-9% (w/w) resin acids.

5. The method according to claim 1, wherein the saponified tall oil fatty acid comprises 5-9% (w/w) resin acids.

6. The method according to claim 1, wherein the saponified tall oil fatty acid is dried.

7. The method according to claim 1, wherein the resin acids are selected from a group consisting of abietic acid, dehydroabietic acid, levopimaric acid, neoabietic acid, pimaric acid, isopimaric acid and combination thereof.

8. The method according to claim 1, further comprising the step of combining the feed supplement with a carrier, wherein the carrier comprises sugar beet pulp.

9. The method according to claim 1, further comprising the step of combining the feed supplement to a feed.

10. The method according to claim 9, wherein the concentration of the feed supplement is 0.005 to 1 kg/ton dry weight of the total amount of the feed.

11. The method according to claim 9, wherein the concentration of the feed supplement is 0.01 to 0.1 kg/ton dry weight of the total amount of the feed.

12. The method according to claim 1, further comprising the steps of combining the feed supplement with a carrier thereby forming a supplement/carrier complex, wherein the supplement/carrier complex is dried having at least 375 grams of tall oil fatty acid soap/kg.

13. The method of claim 1, wherein the microbial population of the animal digestive tract modulates from a homofermentive metabolic route towards a heterofermentive metabolic route.

14. The method of claim 1, wherein the microbial population of the animal digestive tract modulates from a homofermentive metabolic route towards a heterofermentive metabolic route and wherein the modulation of the microbial population improves the feed conversion ratio.

* * * * *